(12) United States Patent
Romero

(10) Patent No.: US 9,278,104 B2
(45) Date of Patent: Mar. 8, 2016

(54) METHODS AND MATERIALS FOR REDUCING MULTIPLE RISK FACTORS ASSOCIATED WITH THE METABOLIC SYNDROME

(75) Inventor: Tim Romero, Sarasota, FL (US)

(73) Assignee: IN Ingredients, Inc., Columbia, TN (US)

( * ) Notice: Subject to any disclaimer, the term of this patent is extended or adjusted under 35 U.S.C. 154(b) by 15 days.

(21) Appl. No.: 13/882,006

(22) PCT Filed: Oct. 26, 2011

(86) PCT No.: PCT/US2011/057833
§ 371 (c)(1),
(2), (4) Date: Apr. 26, 2013

(87) PCT Pub. No.: WO2012/058276
PCT Pub. Date: May 3, 2012

(65) Prior Publication Data
US 2013/0224317 A1     Aug. 29, 2013

Related U.S. Application Data

(60) Provisional application No. 61/406,853, filed on Oct. 26, 2010, provisional application No. 61/438,602, filed on Feb. 1, 2011.

(51) Int. Cl.
*A61K 36/54*     (2006.01)
*A61K 36/00*     (2006.01)
(Continued)

(52) U.S. Cl.
CPC .................. *A61K 31/575* (2013.01); *A23L 1/30* (2013.01); *A23L 1/3002* (2013.01); *A23L 1/302* (2013.01);
(Continued)

(58) Field of Classification Search
IPC .......... A61K 36/00,36/62, 31/045; A01B 12/006
See application file for complete search history.

(56) References Cited

U.S. PATENT DOCUMENTS

| 5,595,743 A * | 1/1997 | Wu | A61K 36/234 |
| | | | 424/728 |
| 6,416,806 B1 * | 7/2002 | Zhou | A23F 5/44 |
| | | | 424/752 |

(Continued)

FOREIGN PATENT DOCUMENTS

| CN | 101524487 A * | 9/2009 |
| KR | 10-0703596 B1 | 3/2007 |

OTHER PUBLICATIONS

Alminger et al. In Vitro Models for Studying Secondary Plant Metabolite Digestion and Bioaccessibility; Compreehsnive Reviews in Food Science and Food Safety; vol. 13, (2004), pp. 413-436.*

(Continued)

*Primary Examiner* — Patricia A Leith
(74) *Attorney, Agent, or Firm* — Dinsmore & Shohl LLP; Weston R. Gould

(57) ABSTRACT

A composition containing *nelumbo* extract reduces and/or eliminates one or more risk factors associated with Metabolic syndrome. The composition also includes optionally one of more components selected from the group consisting of vitamins, cholesterol lowering agents, lipid lowering agents, and glucose lowering agent. Also described is a method of reducing and/or eliminating risk factors associated with Metabolic syndrome in a subject through the administration of the *nelumbo* extract. The *nelumbo* extract supplement is administered orally, intravenously, or subcutaneously. In one embodiment, a daily dose of 10-1,000 mg of the extract supplement is administered to the subject for a period of 6 weeks to 6 months.

7 Claims, 10 Drawing Sheets

(51) Int. Cl.
*A61K 31/575* (2006.01)
*A23L 1/30* (2006.01)
*A23L 1/302* (2006.01)
*A23L 1/305* (2006.01)
*A61K 9/00* (2006.01)
*A61K 9/14* (2006.01)
*A61K 36/62* (2006.01)
*A61K 31/045* (2006.01)

(52) U.S. Cl.
CPC ............. *A23L 1/3004* (2013.01); *A23L 1/3051* (2013.01); *A61K 9/0019* (2013.01); *A61K 9/145* (2013.01); *A61K 31/045* (2013.01); *A61K 36/54* (2013.01); *A61K 36/62* (2013.01); *A23V 2002/00* (2013.01)

(56) References Cited

U.S. PATENT DOCUMENTS

| | | | |
|---|---|---|---|
| 6,602,526 | B2 | 8/2003 | Riley |
| 7,338,671 | B2 * | 3/2008 | Golz-Berner ............ A61K 8/25 424/725 |
| 7,662,413 | B2 | 2/2010 | Wang et al. |
| 2003/0180395 | A1 * | 9/2003 | Bueter ......................... 424/725 |
| 2005/0244441 | A1 * | 11/2005 | Courtois ............... A61K 8/042 424/401 |
| 2005/0255077 | A1 * | 11/2005 | Golz-Berner ............ A61K 8/25 424/74 |
| 2006/0013361 | A1 * | 1/2006 | Fehre et al. ...................... 378/55 |
| 2006/0051435 | A1 * | 3/2006 | Udell .................... A23L 1/3002 424/725 |
| 2006/0068005 | A1 * | 3/2006 | Ross .................... A61K 9/0056 424/464 |
| 2006/0165636 | A1 * | 7/2006 | Hasebe .................... A61K 8/88 424/70.14 |
| 2007/0104805 | A1 * | 5/2007 | Udell ................... A61K 31/202 424/725 |
| 2010/0227007 | A1 | 9/2010 | Romero et al. |

OTHER PUBLICATIONS

De Smet et al. Herbal Remedies; The New England Journal of Medicine; Dec. 19, 2002, vol. 347, Issue 25, p. 2046, 11 pages.*
Dutta Phytosterols As Functional Food Components and Nutraceuticals; 2004, Marcel Dekker, Inc.; Basel, Switzerland, p. 206.*
Leonard et al. A Three-Dimensional Coculture of Enterocytes, Monocytes and Dendritic Cells to Model Inflamed Intestinal Mucosa In Vitro; Molecular Pharmaceutics; vol. 6, No. 6, pp. 2103-2119.*
H.B. MacPhillamy: Drugs From Plants; Plant Science Bulletin, Botanical Society of America, vol. 9, No. 2, Apr. 1963.*
Phillipson, J. New Drugs From Nature—It Could Be Yew; Phytotherapy Research 13 (1999) pp. 2-8.*
Raskin et al. Can an Apple a Day Keep the Doctor Away? Current Pharmaceutical Design, 2004, 10, 3419-3429.*
Revilla et al. Comparison of Several Procedures Used for the Extraction of Anthocynains From Red Grapes; J. Agric. Food Chem. 1998, 46, pp. 4592-4597.*
Thomas et al.: Examining Phytosterols in Nuts and Seeds for the Usda National Nutrient Database for Standard Reference; Online, URL< http://www.nutrientdataconf.org/pastconf/ndbc31/3-1_thomas.pdf> 24 pages, accessed Oct. 10, 2014.*

* cited by examiner

METHODS AND MATERIALS FOR REDUCING MULTIPLE RISK FACTORS ASSOCIATED WITH THE METABOLIC SYNDROME

CROSS REFERENCE TO RELATED APPLICATIONS

This application depends from and claims priority to PCT/US2011/057833, filed Oct. 26, 2011, which claims priority to U.S. Provisional Application No. 61/406,853, filed Oct. 26, 2010, and U.S. Provisional Application No. 61/438,602, filed Feb. 1, 2011, the contents of each of which are incorporated herein by reference.

FIELD OF THE INVENTION

The present invention generally relates to the use of extracts of *Nelumbo nucifera* as a preventive, alleviative or remedy for reducing two or more risk factors associated with the metabolic syndrome, and in particular to reducing both apolipoproteins and inflammation and improving markers of insulin sensitivity.

BACKGROUND OF THE INVENTION

Metabolic syndrome is a metabolic disease characterized by the presence of several of the following risk factors: hyperglycemia, hypertension, low high-density lipoprotein (HDL), high low-density lipoprotein (LDL), high triglyceride, and abnormal body mass index (BMI), micro-albuminuria, endothelial dysfunction, pro-thrombotic state, and inflammatory process. Although not all these criteria need to be met before a diagnosis of the disease may be found, three occurrences of these symptoms may be found indicative of the syndrome.

It is estimated that over 22% of the adult U.S. population have metabolic syndrome and the incidence is rapidly increasing. Old age, postmenopausal status, ethnicity, higher body mass index, smoking, low household income, high carbohydrate intake, and physical inactivity all have been connected with the increased odds of the onset and or deterioration of metabolic syndrome. An additional 12 million adults will likely develop the syndrome as a result of aging alone by 2022.

A single cause at the molecular level cannot be traced to the origin of metabolic syndrome. However, increasing evidence suggests the disease originates from both insulin resistance and activation of vascular inflammatory mechanisms related to increased oxidative stress. For example, insulin resistance results in preferential metabolism of free fatty acids, which leads to reduced glucose utilization. Insulin resistance is identified in children prior to the development of the dyslipidemia, hypertension and hyperglycemia that occur later in life. As one ages, pancreatic beta cell exhaustion is not able to meet insulin resistance demands, and this might eventually lead to the progression of metabolic disturbance including dyslipidemia, hypertension, etc. On the other hand, the infiltration of adipose tissue by inflammatory macrophages has been indicated as a common feature of obesity. Adipose mass, as measured by weight, body mass index (BMI) or visceral obesity, correlates quantitatively with genetic expression of macrophages that produce inflammatory mediators and markers. Other distinct factors and causes are also involved.

All in all, the treatments for metabolic syndrome vary greatly. Many times, a person diagnosed with several risk factors as discussed above would be prescribed a low fat diet, exercise regime, and pharmaceutical intervention including a host of drugs to individually combat issues with cholesterol, blood pressure, glucose, and body weight. Due to the complicated nature of such therapy, compliance is often low.

Therefore, and in view of the fact that metabolic syndrome is distinguishable in cause and effect from diabetes, prior studies do not teach a treatment for pathological states such as hypertension and hyperglycemia in subjects who are not already diabetic; nor do they support a method to concurrently reduce and improve two to three or more risk factors associated with the metabolic syndrome even in diabetic subjects. Furthermore, prior studies fail to provide a useful teaching on how to eliminate a risk factor or reverse these metabolic conditions in people that have not fully developed any disease state.

To date, prior studies have not provided any therapeutic materials that can specifically address metabolic syndrome, nor the mechanisms leading up to the development of the metabolic syndrome. Therapies have been directed to the treatment of specific features of the syndrome on an individual basis, and not to any holistic therapy. As will be explained in detail, the present invention recognizes that particular *Nelumbo*-derived compositions are effective in simultaneously controlling multiple pathologies and pathways leading to the development of metabolic syndrome. Furthermore, the therapeutic compositions and processes described herein are simple to implement and conducive to good patient compliance.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

The present invention relates to a composition containing an extract of *Nelumbo nucifera* and a method of using the composition to prevent, alleviate, or treat two or more risk factors associated with metabolic syndrome in a subject. In particular, the invention relates to methods of reducing apolipoproteins and inflammation while also enhancing insulin sensitivity in a subject.

DETAILED DESCRIPTION OF THE INVENTION

Figure 1:
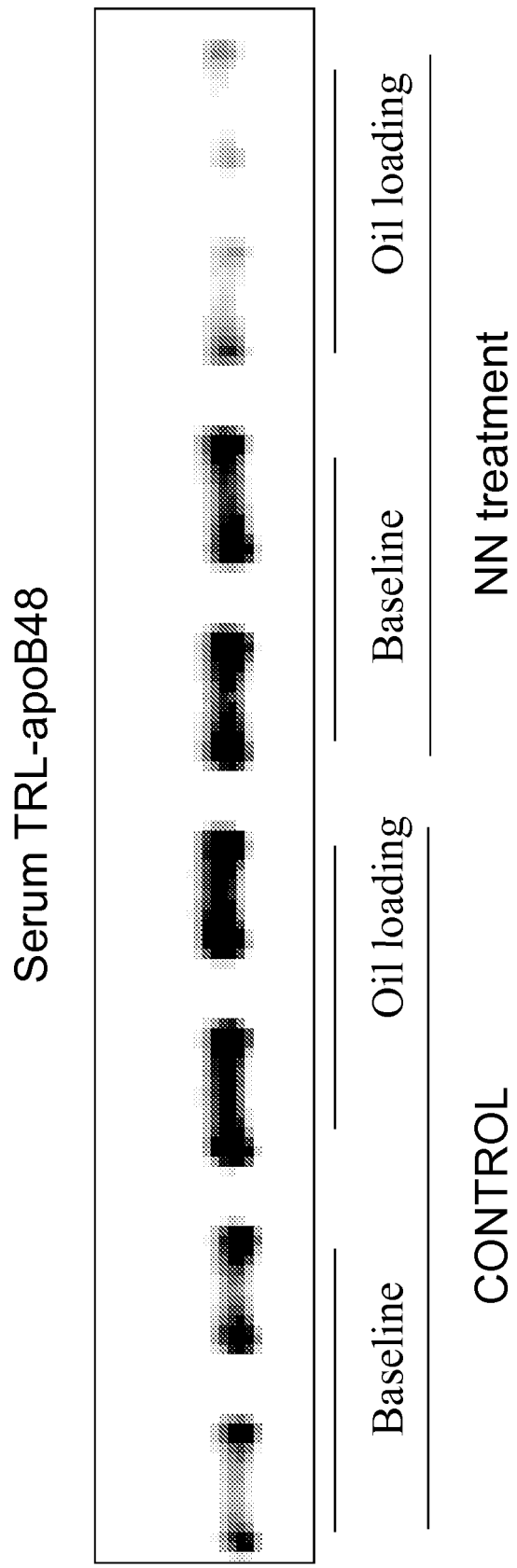
FIG. 1 is an immunoblot for serum TRL-apoB48 from rats administered a control or an extract of *Nelumbo nucifera*.

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes are described as an order of individual steps or using specific materials, it is appreciated that described steps or materials may be interchangeable such that the description of the invention includes multiple parts or steps arranged in many ways as is readily appreciated by one of skill in the art.

The compositions and processes of the claims have utility for the reduction, amelioration, correction, alteration, or other beneficial effect that is related to correction of one or more risk factors for metabolic syndrome. Among the nearly infinite possible compositions for the therapeutic or preventative treatment of metabolic syndrome or risk factors of metabolic syndrome, the inventors unexpectedly discovered that compositions including *Nelumbo nucifera* or an extract thereof are capable of reducing one or more risk factors of this ever increasingly common syndrome. The inventors present for the first time evidence of beneficial effects of these unique formulations.

*Nelumbo* is a fairly common plant. *Nelumbo* is an aquatic perennial, but if its seeds are preserved under favorable circumstances they may remain viable for many years. *Nelumbo* was native to a huge area from modern Vietnam to Afghanistan, being spread widely as an ornamental and food plant. Today it is rare or extinct in the wild in Africa but widely naturalized in southern Asia and Australia where it is commonly cultivated in water gardens. The roots of *Nelumbo* are planted in the soil of a pond or river bottom, while the leaves float on top of the water surface. It grows in lakes and swamps, as well as areas subject to flooding.

Compounds present in *Nelumbo* illustratively include various saponins, flavonoids, quercetin, isoquercitin and many others. Flavonoids may be extracted from *Nelumbo* and isolated, and, optionally, derivatized. In some embodiments of the invention, the dietary supplement includes flavonoids.

The inventors found that the mRNA levels of the insulin signaling pathway components insulin receptor (IR), insulin receptor substrate 1 (IRS-1), insulin receptor substrate 2 (IRS-2), thymoma viral proto-oncogene 1 (Akt1), phosphatidylinositol 3 kinase, regulatory subunit 1 (PI3Kr1), and Src homology 2 domain-containing transforming protein 1 (SHC1) in the enterocytes of chow-fed hamsters were significantly enhanced by *Nelumbo*. Extracts of *Nelumbo* also inhibit SHC1 expression in these cells.

Additionally, IR, IRS-1, IRS-2, Akt1, PI3Kr1, and SHC1 in enterocytes of hamsters fed a high-fructose diet induce insulin resistance. *Nelumbo* extracts significantly improve the impaired mRNA overexpression of IR, IRS-1, IRS-2, Akt1, and PI3Kr1β, and inhibits SHC1 expression in enterocytes of these animals. Thus, the inventors identified a direct correlation between the mRNA levels for proteins involved in enhanced insulin signaling and *Nelumbo* extract administration.

As used herein a "risk factor" is a pathological disorder that contributes to the diagnosis of metabolic syndrome in a human.

A "flavonoid" refers to a group of chemical substances found in plants. Flavonoids are polyphenolic compounds ubiquitous in nature of which over 4000 exist. They are categorized according to chemical structure, into flavonols, flavones, flavanones, isoflavones, catechins, anthocyanidins and chalcones.

A "pre-diabetic" subject refers to one whose fasting blood glucose level is in a medically acceptable range recognized by common medical practices. Although the normal range may depend further on other aspects of the subject, such as age and sex, a fasting blood glucose level of 100-125 mg/dl (6.9 mmol/L) may be regarded as "pre-diabetic".

A used herein, an "active ingredient" refers a component present in a *Nelumbo* extract that renders, directly or indirectly, the intended effect of the extract.

"Insulin sensitivity" refers to the body's ability to process glucose. Multiple methods are known to those skilled in the art to calculate one's insulin sensitivity.

As used herein, the terms "subject" or "patient" are treated synonymously and are defined as any organism capable of displaying one or more risk factors for human metabolic syndrome, an indicator of one or more such risk factors, or serve as a model for one or more risk factors of metabolic syndrome. A subject illustratively includes a mammal such as humans, non-human primates, murine, equine, and a cell.

Metabolic syndrome is a metabolic state. It is also interchangeably known as Syndrome X. As defined by National Cholesterol Education Program's Adult Treatment Panel III (NCEP-ATP-III), metabolic syndrome represents a collection of risk factors including hypertension, dyslipidemia, obesity, and hyperglycemia. It is noted that not all the risk factors need to be present for a diagnosis of metabolic syndrome to be made. It is known to the art that a finding of three or more of the following risk factors is indicative of the presence of metabolic syndrome.

1) Central obesity as measured by waist circumference: Men—greater than 40 inches; Women—greater than 35 inches.
2) Fasting blood triglycerides greater than or equal to 150 mg/dL.
3) Blood HDL (high density lipoprotein) cholesterol: Men—less than 40 mg/dL; Women—less than 50 mg/dL.
4) Blood pressure greater than or equal to 130/85 mmHg.
5) Fasting glucose greater than or equal to 110 mg/dL.

Although modern pharmaceutical research has made it almost a certainty to locate a medicinal therapy for each risk factor, a combination treatment aimed to target two to three or more risk factors may bring many unnecessary side effects, and may function by an unproven molecular mechanism. Therefore, it is desirable to have a method and a composition to improve multiple risk factors or the pathways involved in these risk factors simultaneously.

An inventive composition and process of ameliorating two or more risk factors of metabolic syndrome are provided. An inventive composition illustratively includes one or more portions of a *Nelumbo* plant, extracts of one or more portions of a *Nelumbo* plant, or a derivative of an extract of a *Nelumbo* plant or portion thereof. Compositions are provided that include *Nelumbo nucifera* (NN) or an extract thereof. Compositions that do not include an extract as the primary active component are based on rough preparations of *Nelumbo nucifera*. Rough preparations are optionally prepared by drying, grinding, chopping, or otherwise exposing a surface area relative to the raw NN that is found in nature. These processes provide a composition that can be more readily packaged into a delivery device (e.g. capsule, bag, etc.) for administration to a subject.

Some embodiments include one or more extracts of NN. Extracts may be prepared by various methods with the proviso that the extracts include 1 percent or more of active component such as flavonoids. In some embodiments, the extracts include between 1 and 30% flavonoids. Optionally, the extracts include between 5 and 15 percent flavonoids. Optionally, extracts include 10% flavonoids. Extraction parameters such as water quality, heating temperature, drying temperature, heating time, drying time, and filtering processes all contribute to the quality and efficiency of the extraction process as well as the level of active flavonoids present in the final compositions. Water quality directly affects the concentration of active compounds. Heating time also affects the thickness of extraction mixture, which then has a direct impact on the downstream filtering process. Lastly, drying temperature may vary from 75° C. to 120° C. depending on what other extraction parameters are also used.

In one illustrative extraction procedure, raw *Nelumba nucifera* plant is ground to provide a powder material. The resulting powder materials are extracted with 10 volumes hot water (90° C.) for 60 min and then stored at 4° C. The extracted material is centrifuged to remove insoluble matter. The material is then dried to a powder. The resulting powder is optionally sifted to provide particles with a size that will pass through a 40# sieve. The powder is optionally sterilized. In some embodiments, the extract is concentrated in a distillation vessel to improve yields of flavonoids. A concentrated material is optionally subjected to extract purification by solvent wash or by liquid-liquid extraction to further improve the yields of the flavonoids.

Some embodiments include one or more extracts of NN. Extracts are prepared by various methods. Extracts are optionally prepared with ethanol or other organic solvent. In some embodiments, the plant material undergoes both aqueous and solvent extraction. The process is similar to that of an aqueous extraction except illustratively with a ratio 70:30 alcohol:water. Alcohol is optionally ethanol. Other ratios such as 50:50, or more or less relative water or organic solvent, are also operable. This may in fact increase the yield output, particularly of the flavonoid concentration.

Regardless of the natural source location or portion of the *Nelumbo* plant, the inventive compositions are optionally extracted with polar aprotic solvents such as methylene chloride, $C_1$-$C_6$ alcohols, $C_3$-$C_6$ ketones, tetrahydrofuran, formamid, $C_3$-$C_{16}$ esters, nitrogen-containing heterocyclics, and combinations thereof. In particular, it is appreciated that crude extraction from macerated plant material in a first solvent, followed by a secondary extraction from the inventive acid-containing fraction serves to further purify the inventive materials. A water or methylene chloride initial extraction followed by a methanol or ethanol extraction is exemplary of such extraction processes (Juan et al., J. Nutri., 136, p. 2554, first column, ¶¶1-2, 2006).

Heating time affects the level of active component and also affects the thickness of extraction mixture which then has a direct impact on the downstream filtering process. Lastly, drying temperature optionally varies from 75° C. to 120° C., optionally from 50° C. to 120° C., depending on what other extraction parameters are also used. Drying is appreciated to be operable at ambient temperature.

In some embodiments, 50 g clean leaf of the *Nelumbo nucifera* plant is ground into small particles or powder. The powder or particles are mixed with 1000 ml distilled water in a suitable flask. The mixture is let stand at room temperature for about 0.5 hour. Additional water may be added is in the range of 1:20 to 1:2000. Too little water may render the mixture too thick for extraction. However, too much water increases drying time. Then the water mixture is heated while being stirred through the use of a magnetic heat stirrer. The temperature and extraction time are crucial to the concentration efficiency of the extract. The extraction process is optionally no longer than one hour. In some embodiments the ground plant material is heated for 15-20 minutes bringing to a boil, simmering (95° C.) for 20-30 minutes optionally while stirring constantly. The boiling time is typically controlled at about 20-25 minutes following heating. The mixture is optionally cooled and stored at 4° C. overnight.

In other embodiments, the extraction solution is filtered through a filter paper to remove any solid debris. If the solution is too thick for the filter paper, the removal of solids from the solution is optionally done with the use of centrifugation. The resulting supernatant is optionally filtered through medium speed filter paper. The resulting solids are optionally dissolved in 200 mL distilled water for a second extraction. The liquid solution containing the solids is mixed and heated for 30 minutes at 50-100° C., optionally 80-90° C., and then is filtered.

In other embodiments, the first and second extraction solutions are combined together and poured onto nonstick tray and allowed to dry at 50-100° C., optionally 80-90° C. Vacuum-spray dry equipment is optionally used for the drying procedure. The resulting dry extract powder is weighed. The sample and water ratio, heat time, volume of water in the second extraction may vary depending on the amount of the raw material used for extraction. The dry NN extract powder is collected and weighed. The extraction ratio is calculated by the following equation:

$$\% = w/20 \times 100\% \text{ where}$$

w is the weight (g) of the NN extract powder.

The NN, NN extract, or derivative of NN extract in the inventive compositions is present in an amount sufficient alter two or more risk factors for metabolic syndrome. In some embodiments two risk factors are altered. Optionally, three risk factors are altered. Optionally, four risk factors are altered. Optionally, 5 risk factors are altered. Optionally, 6 risk factors are altered. In some embodiments, two or more risk factors are altered. Optionally, all known risk factors are altered. Some compositions according to the invention illustratively include from about 1 mg to about 1000 mg of NN, NN extract, or derivative of a NN extract per gram.

A composition optionally also includes an extract of cinnamon. Illustrative examples of a cinnamon extract include that sold under the name CINNULIN PF, by Integrity Neutraceuticals, Spring Hill, Tenn. Illustrative examples of methods of manufacture of a cinnamon extract can be found in U.S. Pat. No. 6,200,569, and U.S. Patent Application Publication No. 2007/0237845. When an extract of cinnamon is present, it is optionally present in an amount appropriate to deliver a dosage is in the range of 10-1,000 mg of equivalent of dry cinnamon powder per day.

A composition of NN, an extract of NN, or a derivative of an extract of NN optionally further includes creatine, a precursor of creatine, or a derivative of creatine. The chemical name for creatine is methylguanidino acetic acid. The inventive compositions optionally include creatine or a derivative thereof, for example a hydrate, salt or ester thereof. Commercially available creatine derivatives include creatine monohydrate, other creatine hydrates, creatine citrate, and creatine pyruvate. The creatine employed in the compositions of the present invention optionally includes creatine monohydrate, commercially available from various sources. Optionally the creatine, creatine monohydrate or other creatine derivative is a pharmaceutical-grade material. Creatine derivatives illustratively include: creatine monohydrate and other hydrates; creatine salts such as creatine citrate; creatine esters; phosphorylated creatine; and creatine pyruvate. Creatine precursors illustratively include: glycocyamine; guanidineacetic acid; and the amino acids arginine, glycine, and methionine.

Specific illustrative examples of creatine derivatives include: creatine monohydrate; creatine anhydrous; creatine taurinate; creatine pyruvate; creatine ethyl ester; dicreatine malate; creatine deconate; creatine citrate; creatine phosphate; glycocyamine; creatine alpha ketogluturate; creatine ketoisocaproate; and creatine magnesium chelate. In some embodiments of the invention, the dietary supplement includes creatine monohydrate.

The inventive composition optionally includes carbohydrate illustratively: simple sugars such as the monosaccharides glucose, fructose, ribose, mannose, galactose, dextrose, and the like; or complex sugars such as sucrose, maltose, cellobiose, lactose, raffinose, and the like. It is appreciated that larger polymers of monosaccharide units are similarly operable in the invention. Illustrative examples include amylase, amylopectin, cellulose, chitin, as well as heteromeric polysaccharides. In some embodiments, saccharides are pharmaceutical grade. Sources for saccharides are well known in the art.

Inventive compositions optionally contain from about 100 mg to about 500 mg of creatine, creatine derivative, or creatine precursor per gram. In some embodiments carbohydrate is present from about 100 mg to about 900 mg of per gram of dietary supplement.

The inventive compositions optionally include a chromium compound. Chromium is a constituent of a biologically active compound, the glucose tolerance factor (GTF), found in foods such as organ meats, whole grains, cheese, mushrooms and brewer's yeast. Various chromium compounds are optionally included in the inventive compositions, and in amounts effective to improve insulin efficiency. An illustrative chromium compound is chromium picolinate, which is optionally present from about 50 micrograms to about 500 micrograms per 100 grams of supplement. Additional components for the inventive compositions illustratively include additional minerals such as magnesium, potassium, phosphorous, salts thereof, or mixtures thereof in amounts conventional in the art, for example, from about 0.01 mg to about 100 mg per gram of supplement. The inventive compositions optionally contain ascorbic acid (vitamin C), for example in amounts equal to or exceeding the recommended minimum daily requirements. Optionally included is beta-hydroxy, beta-methyl butyrate (HMB), in amounts known in the art.

Optionally, the inventive composition is combined with one or more protein sources. Such sources may include whey protein isolate, whey protein concentrate, free form amino acids, buckwheat protein, soy protein isolate or concentrate, milk protein isolate or concentrate, micellar casein, calcium or other caseinate proteins, rice protein, or any combination of the above. Optionally, the protein contains quantities of essential amino acids.

Depending on the intended mode of administration, the extract supplement can be in pharmaceutical compositions in the form of solid, semi-solid or liquid dosage forms, such as, for example, tablets, suppositories, pills, capsules, powders, liquids, or suspensions, and may be provided in unit dosages suitable for a single administration. Time release preparations are specifically contemplated as effective dosage formulations. The compositions will include an effective amount of the selective active agent such as NN, and extract of NN, or a derivative of an extract of NN, in combination with a pharmaceutically acceptable carrier and, in addition, may include other medicinal agents, pharmaceutical agents, carriers, or diluents.

For solid compositions, conventional nontoxic solid carriers include, for example, pharmaceutical grades of mannitol, lactose, starch, magnesium stearate, sodium saccharine, talc, cellulose, glucose, sucrose and magnesium carbonate. Liquid pharmaceutically administrable compositions can, for example, be prepared by dissolving or dispersing an active compound with optimal pharmaceutical adjuvants in an excipient, such as water, saline, aqueous dextrose, glycerol, or ethanol, to thereby form a solution or suspension. If desired, the pharmaceutical composition to be administered may also contain minor amounts of nontoxic auxiliary substances such as wetting or emulsifying agents, pH buffering agents, for example, sodium acetate or triethanolamine oleate. Actual methods of preparing such dosage forms are known, or will be apparent, to those skilled in this art; for example, see Remington's The Science and Practice of Pharmacy ($20^{th}$ Edition).

For oral administration, fine powders or granules may contain diluting, dispersing, and/or surface active agents, and may be presented in water, a syrup, in capsules, sachets, in the dry state, or in a non-aqueous solution or suspension wherein suspending agents may be included, in tablets wherein binders and lubricants may be included, or in a suspension. Where desirable or necessary, flavoring, preserving, suspending, thickening, or emulsifying agents may be included. Tablets and granules are exemplary oral administration forms, and these may be coated.

The NN, NN extract, or derivative of an NN extract containing dietary supplement according to the present invention is optionally combined with one or more other components. Such components include, but are not limited to, vitamins (such as vitamin A, vitamin B, vitamin C, vitamin D, or vitamin E), a glucose lowering agent (such as glucose receptor stimulator, insulin sensitizer, glucogen synthesis stimulator, glucose uptake facilitator). Illustrative components include corosolic acid, cinnamon or cinnamon extracts, momordica, cecropia or any other agent to act on the glucose system, a blood pressure lowering agent (such as α-blocker, β-blocker, angiotensi II receptor antagonist), green tea polyphenols (such as epigallocatechin gallate), and lipid lowering agent, or a modifier of cholesterol levels such as cholesterol synthesis inhibitor, or phytosterols such as policosanol, β-sitosterol, campesterol, stigmasterol, sitostanol, etc.

The extract dietary supplement according to the present invention is available as an oral dietary supplement taken in a form such as tablets, granules, pills, powders, capsules, chewables, or liquid medicinal drinks.

The composition is optionally administered orally, parentally, or intravenously by intramuscular, intraperitoneal, or transdermally injection. Injectables may be prepared in conventional forms, either liquid solutions or suspensions, solid forms suitable for solution or prior to injection, or as suspension in liquid prior to injection or as emulsions. The dose of the dietary supplement composition may vary depending on the age, weight, or general condition of the user. Several forms of administration are operable herein illustratively including ingestion, inhalation, or injection. Typical administrations are by oral ingestion. Ingestion is optionally with or without other food.

The amount of the inventive composition administered to the diet or otherwise of a subject varies depending on the desired effect, the body weight and characteristics of the subject, and the like. Those of ordinary skill in the art recognize methods of administration for particular desired outcomes. Typical dosages of the inventive composition are about 10 mg to about 1,000 mg of NN, NN extract, or a NN extract derivative. In some embodiments, a dosage includes from about 2 g to about 25 g of creatine, creatine derivative, creatine precursor. In some embodiments where an inventive composition includes creatine, a creatine derivative, or a creatine precursor a loading dose is used. A loading dose illustratively includes about 20-25 grams of creatine, a creatine derivative, or a creatine precursor administered daily for 5 days. This is optionally followed by a steady maintenance dose of creatine, a creatine derivative, or a creatine precursor from about 2-10 grams per day.

Typical dosages of the inventive composition are from about 10 mg to about 1,000 mg of NN, NN extract, or NN extract derivative. In some embodiments, NN, NN extract, or NN extract derivative are administered in an amount from about 250 mg to about 1,000 mg.

The dietary supplement according to the present invention is optionally formulated as a food additive. Examples supplement formulations for addition to foods include a liquid, semi-liquid, solid, paste, or jelly form. In some embodiments, a dietary supplement composition is administered as a liquid, optionally an aqueous liquid.

The extracts of NN have a utility to reduce, alleviate, remedy, or otherwise alter two or more risk factors in a subject categorized as having metabolic syndrome according to the criteria set forth by NCEP-ATP-III. The disorders manageable by the extract formulation include, but are not limited to, abnormalities in fasting blood glucose (FBG), body mass index (BMI), SBP, high density lipoprotein (HDL) level, low density lipoprotein (LDL) level, triglyceride level, oxidative stress, and inflammatory state. Moreover, the pathways leading to the development of these risk factors are targeted in multiple ways.

One feature of the composition is its ability to reduce, alleviate, or remedy disorders is not necessarily dependent upon the subjects being diabetic. The compositions also exert desirable effects on those that may be at risk for developing metabolic syndrome. According to some embodiments of the invention, NN, an extract of NN, or a derivative of an extract of NN is administered to a subject that is non-diabetic.

In some embodiments of the inventive processes, greater amounts of the inventive composition are initially administered to the subject's diet for acute effect (loading period), followed by a maintenance period during which the amounts of inventive composition are relatively decreased. The loading period optionally extends several weeks. In some embodiments, a loading period is one, two, three, four, five, six or more weeks. Optionally, a loading period is from one day to six weeks or more, as well as any period therebetween as desired by the subject, trainer, physician, or other depending on the desired outcome and rapidity of desired results. Once a desired reduction, amelioration, or alteration of two or more risk factors for metabolic syndrome have been obtained, lower amounts of the inventive composition, illustratively a maintenance period, are optionally administered to the subject to maintain or improve the results.

A significant underlying etiology of metabolic syndrome, dyslipidemia, is characterized as a collection of phenotypes that includes increased free fatty acids, elevated serum triglycerides, decreased HDL cholesterol, and elevated LDL cholesterol. Low HDL cholesterol, with a shift to smaller size HDL, is common in metabolic syndrome and is due to triglyceride enrichment of HDL, increased HDL degradation by hepatic lipase and increased apolipoprotein AI catabolism. A therapeutic strategy for dyslipidemia treatment should be to reduce LDL cholesterol to 60-70 mg/dL, increase HDL cholesterol to 40 mg/dL in men and 50 mg/dL in women, and to reduce triglyceride levels to less than 150 mg/dL. Appropriate combinations of nutritional supplements and lipid lowering drugs in addition to the inventive compositions and dietary supplements containing such may work in concert to help achieve these goals. It is known in the art that additional supplements helpful in reducing dyslipidemia associated symptoms include niacin, marine lipids, policosanol, plant sterols, soy, green tea, flax, tocotrienols, pantothenic acid, etc. As such, these or other supplements are optionally included in a dietary supplement including NN, and extract of NN, or a derivative of an extract of NN. Administration of an inventive composition optionally achieves one or more of reducing LDL cholesterol to 60-70 mg/dL, increasing HDL cholesterol to 40 mg/dL in men and 50 mg/dL in women, or reducing triglyceride levels to less than 150 mg/dL, alone or in combination with an alteration of one or more other risk factors characterizing metabolic syndrome to desirable levels.

The composition of lipoprotein make up is of key importance when determining the overall LDL profile. Apolipoproteins are "lipid-binding proteins which are the constituents of the plasma lipoproteins, sub-microscopic spherical particles that transport dietary lipids through the bloodstream from the intestine to the liver, and endogenously synthesized lipids from the liver to tissues that can store them (adipocytes), metabolize them (muscle, heart, lung), or secrete them (breast)." Of interest is the fact that apolipoprotein B48 is known for its deleterious effects on cardiovascular disease and the transport of LDL to the tissues. Treatment or prevention of one or more determinants of metabolic syndrome, particularly of LDL molecules and prevention of cellular adhesion to cardiovascular and other tissues, is envisioned by administration of an inventive composition.

Variable dosing regiments are operative in the method of treatment. While in some instances, a single dose treatment is effective in producing therapeutic effects, in other instances a treatment period in the range of 6 weeks to 3 months is utilized.

The supplement can be administered: orally; parentally, such as intravenously; by intramuscular injection; by intraperitoneal injection; or transdermally. The exact dose of the supplement required can vary from subject to subject, depending on the age, weight, general condition of the subject, the severity of risk factors associated with metabolic syndrome, the mode of administration, and the like. An appropriate dose is readily determined by one of ordinary skills in the art using only routine experimentation given the teachings herein. Generally, dosage is in the range of 10-1,000 mg of equivalent of dry powder per day.

Parenteral administration is generally by injection. Injectables can be prepared in conventional forms, either liquid solutions or suspensions, solid forms suitable for solution or prior to injection, or as suspension in liquid prior to injection or as emulsions.

Various aspects of the present invention are illustrated by the following non-limiting examples. The examples are for illustrative purposes and are not a limitation on any practice of the present invention. It will be understood that variations and modifications can be made without departing from the spirit and scope of the invention. While the examples are generally directed to rats and hamsters, a person having ordinary skill in the art recognizes that similar techniques and other techniques known in the art readily translate the examples to other organisms such as humans.

EXAMPLES

Example 1

Compositions Including an Extract of Nelumbo nucifera 50 g clean leaf of the Nelumbo nucifera plant leaf is ground into small particles or powder. The powder or particles are mixed with 1000 ml (10 volumes) distilled hot water (90° C.) in a suitable flask. The mixture is let stand at room temperature for about 60 minutes. The extracted material is centrifuged to remove insoluble matter. The extraction solution is poured onto nonstick tray and dried at 85° C. The resulting dry material is stored at 4° C.

The extract of Formula A is prepared to include the above extract and the following ingredients to create a dietary supplement of Formula A.
Formula A:

| | |
|---|---|
| Nelumbo nucifera extract | 200 mg |
| Extract of Cinnamon (CINNULIN PF) | 250 mg |
| Phytosterols | 1000 mg |

Example 2

The extract of Example 1 is used to make a dietary supplement of Formula B in the form of a capsule for oral administration.
Formula B:

| | |
|---|---|
| Creatine Monohydrate | 500 mg |
| Nelumbo nucifera extract | 250 mg |
| Total Weight | 750 mg |

Example 3

Affects of Administration of Extracts of Nelumbo nucifera to Subjects

The effects of NN extract on apolipoprotein B48 and FFA levels in fructose-fed rats. The primary objective was to determine the effects of Nelumbo nucifera on intestinal-derived apoB production in insulin resistance-induced by fructose fed animals.

Postprandial elevation of triglyceride-rich lipoproteins (TRLs) is a well-recognized feature of diabetic dyslipidemia and includes the accumulation of intestinally derived apoB48-containing chylomicrons. To investigate the acute effect of NN extract on apolipoprotein B48-containing lipoproteins in fat-fed state, four-week fructose-fed rats were randomly divided into two groups: saline; or 100 mg/kg of body weight NN extract of Formula A treatment (4 or 5 rats in each group). An oral olive oil loading was performed on overnight fasted rats. Blood samples were drawn from the tail vein at baseline and 120 min after fat loading from saline-and NN-treated fructose-fed rats. Triglyceride rich lipoproteins were immunoblotted, using an anti-hamster apoB antibody. As shown in FIG. 1, acute NN treatment inhibits the postprandial apoB48 overproduction in an olive oil loading test in fructose-fed rats.

Example 4

Previous studies have shown that chronic fructose feeding induced significant overproduction of apolipoprotein B48-containing lipoproteins in the fasting state and during steady state fat feeding. Here, we tested the acute effect of NN on apolipoprotein B48-containing lipoproteins in non-fasting state. Twelve-week fructose-fed rats were randomly divided into two groups: saline; and 100 mg/kg (oral) NN extract (Formula A) treatment (4 or 5 rats in each group). An oral olive oil loading was performed on overnight fasted rats. Blood samples were drawn from the tail vein at 2 hours after saline or NN treatment for the production of plasma. Blood samples were drawn from the tail vein at baseline and 120 min after fat loading and kept in tubes containing EDTA. Centrifugation at 13,000×g was performed to separate serum for apoB48 and FFA concentration measurements.

Figure 2:
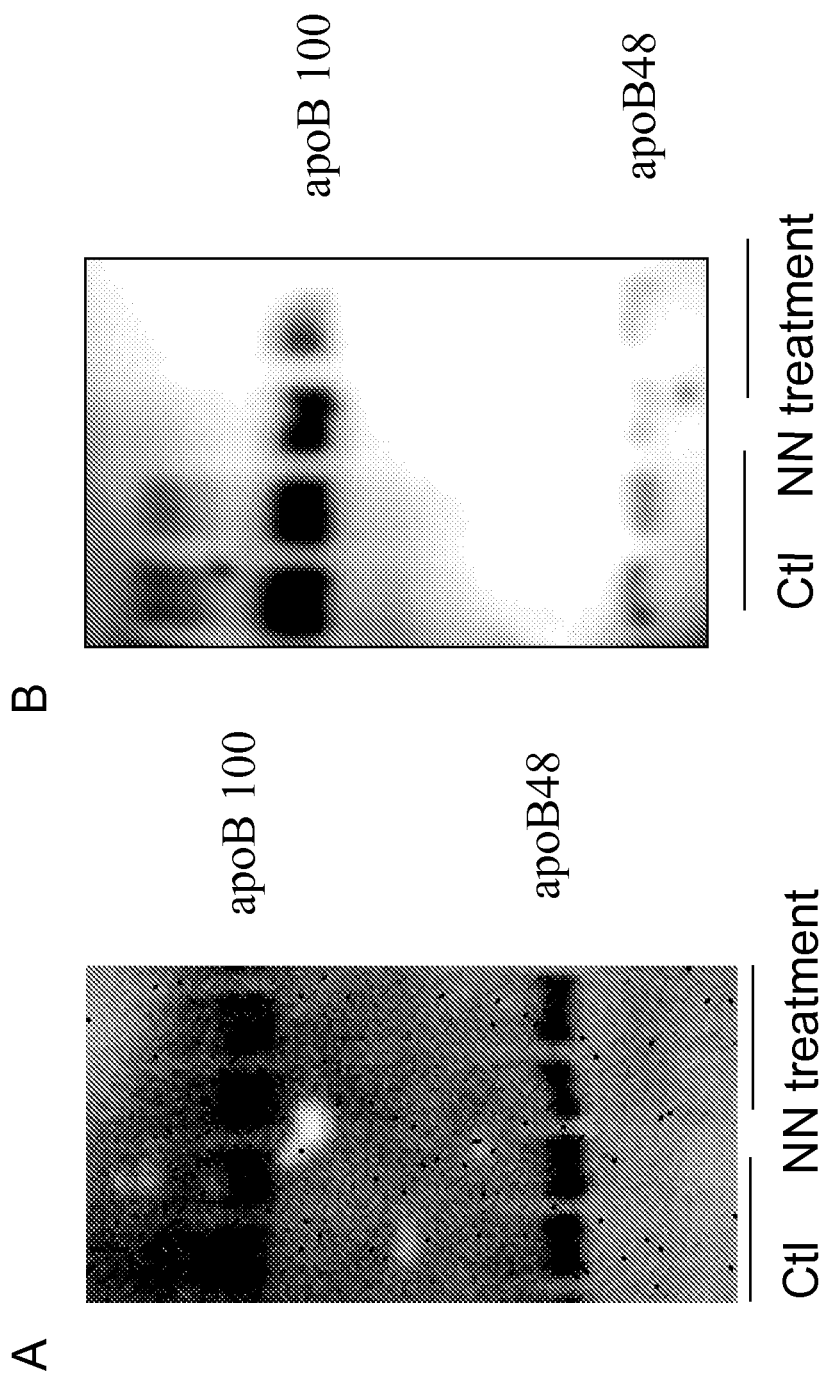
FIG. 2 illustrates the inhibition of ApoB48 in serum from fasted fructose-fed rats (A) or non-fasted 29-week old rats (B) administered an extract of *Nelumbo nucifera*.

The plasma apoB48 levels were visualized by immunoblotting using an anti-hamster apoB primary antibody followed by anti-rabbit horseradish peroxidase secondary antibody. As shown in FIG. 2A, NN treatment significantly inhibits the total apoB48 overproduction in non-fasted fructose-fed rats.

Example 5

Aging is the major risk factor for the development of cardiovascular diseases, the leading cause of morbidity, mortality and disability in western countries. In this example, we used the acute effect of NN on apoB production in maturation-induced insulin resistant rats. 29-week old rats were randomly divided into two groups: saline; and 100 mg/kg (oral) NN extract of Formula A treatment (5 rats in each group). Blood samples were drawn from the tail vein at 2 hrs after saline or NN treatment. The plasma apoB48 levels were visualized by immunoblotting using an anti-hamster apoB primary antibody followed by anti-rabbit horseradish peroxidase secondary antibody. As shown in FIG. 2B, NN treatment significantly inhibits the total apoB48 overproduction in non-fasted 29-week old rats.

Examples 3-5 taken together demonstrate that acute NN treatment significantly inhibits a novel marker of metabolic risk, intestinally-derived apoB48 overproduction in the insulin resistant animals.

Example 6

Figure 3:
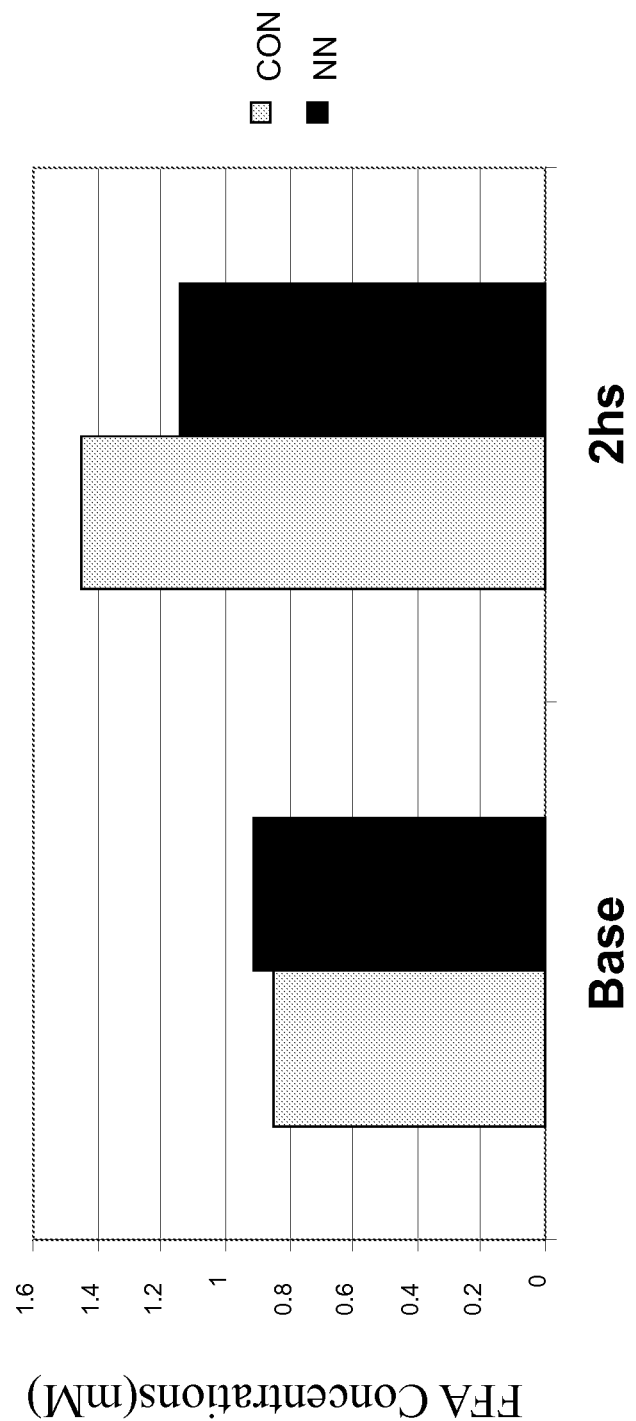
FIG. 3 illustrates that an extract of *Nelumbo nucifera* inhibits the postprandial FFA concentration in fructose-fed rats.
Figure 4:
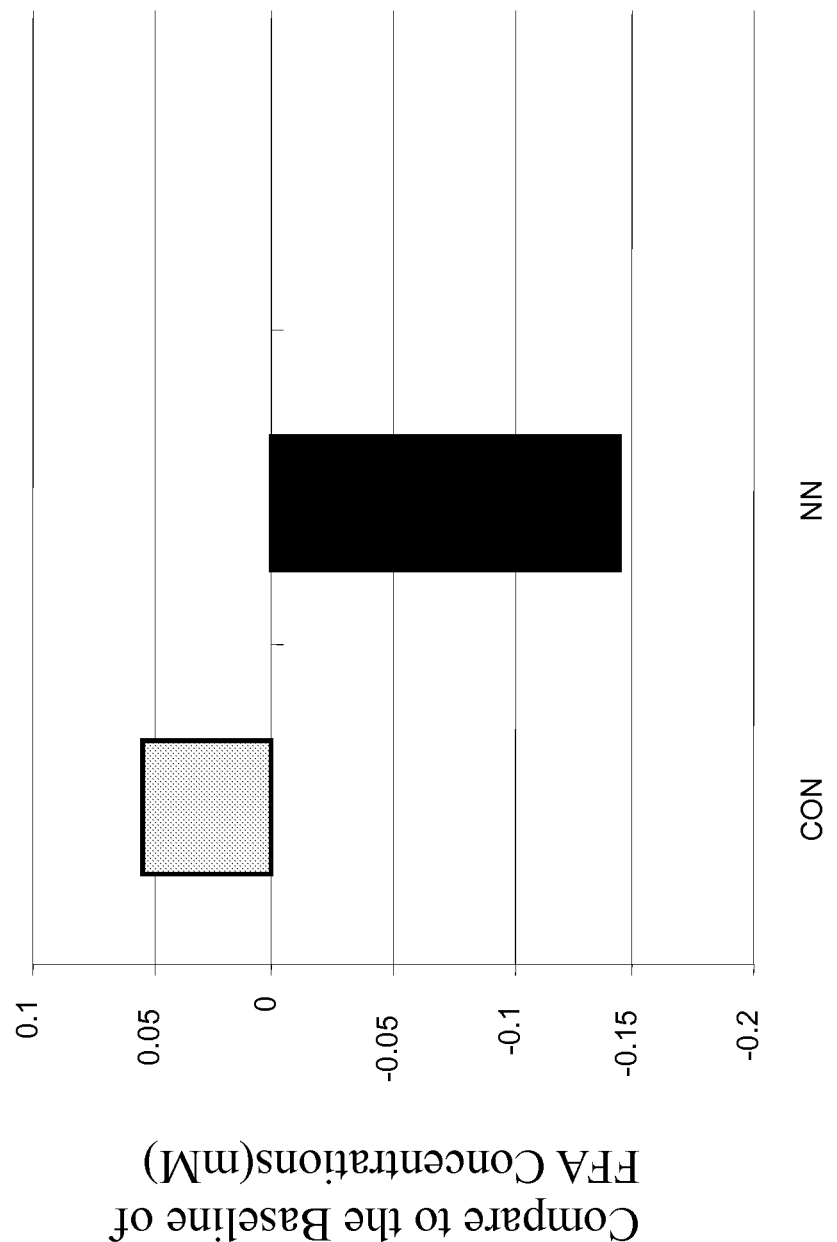
FIG. 4 illustrates that an extract of *Nelumbo nucifera* inhibits the postprandial FFA concentration in non-fasted 29-week old rats.

Free fatty acids (FFA) are believed to be major environmental factor linking obesity to Type II diabetes. Elevated FFA flux in insulin-resistant states and type 2 diabetes play an important role in the pathogenesis of the typical dyslipidemia of these conditions. Furthermore, intestinal lipoprotein production is markedly stimulated by an acute elevation of plasma FFAs in insulin-sensitive hamsters. Here, we tested the acute effect of NN (200 mg/kg) on FFA concentration in fat-fed or non-fasted insulin resistant rats. The samples from animals of Examples 4 and 5 are used to measure FFA. As shown in FIGS. 3 and 4, NN inhibits the postprandial FFA concentration in fructose-fed rats and in non-fasted 29-week old rats.

Example 7

Isolated enterocytes from chow or fructose-fed hamsters with metabolic syndrome induced by a fructose diet were treated with NN extract (100 µg/ml of extract powder dissolved in water) for 0, 30 min, 2 hours, and 4 hours at 37° C. Total RNA was isolated from the enterocytes and reverse transcribed into cDNA. 25 ng of RNA-derived cDNA was used for quantitative real-time PCR assays. The $\Delta C_T$ method of relative quantification was used to determine the fold change in expression. The results represent the percentage mean and the standard deviation from 3-4 repetitions of each sample.

Figure 5:
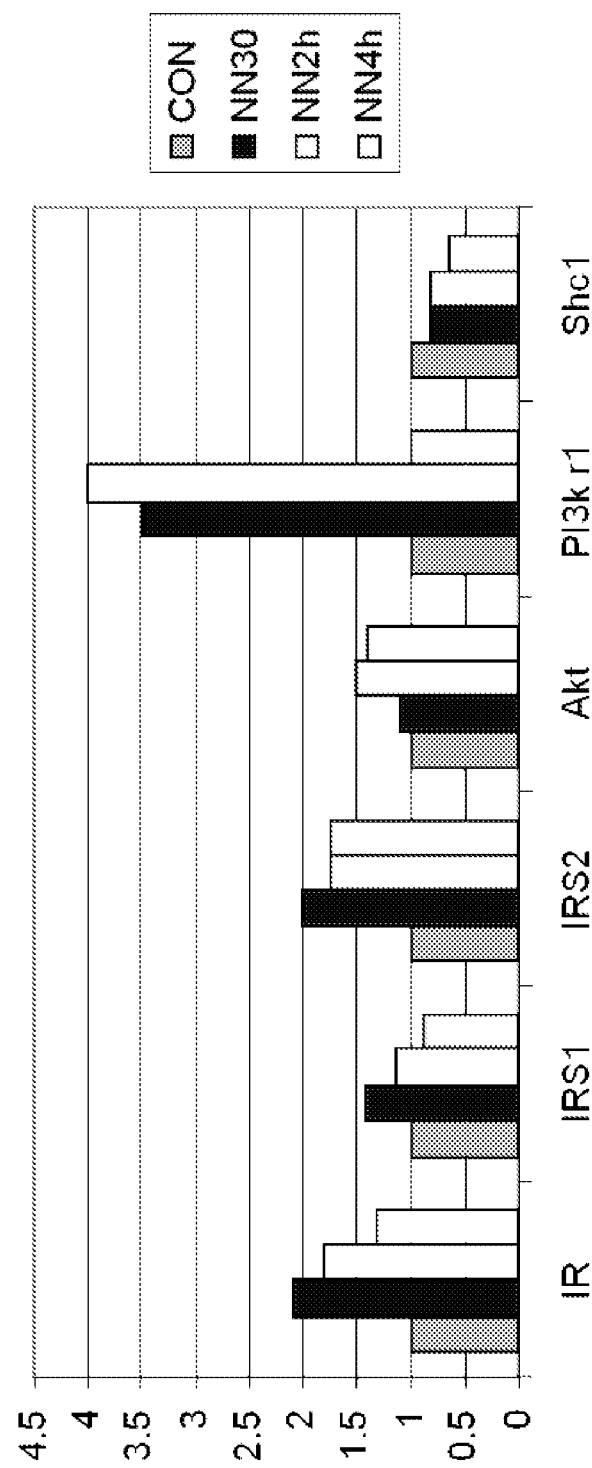
FIG. 5 illustrates that administration of an extract of *Nelumbo nucifera* significantly enhances the mRNA expression of IR, IRS-1, IRS-2, Akt1, PI3Kr1 in enterocytes of chow-fed hamsters, and inhibits SHC1 expression.

The mRNA levels of the following genes coding for insulin signaling pathway components [insulin receptor (IR), insulin receptor substrate 1 (IRS-1), insulin receptor substrate 2 (IRS-2), thymoma viral proto-oncogene 1 (Akt1), phosphatidylinositol 3-kinase, regulatory subunit 1 (PI3Kr1), and Src homology 2 domain-containing transforming protein 1 (SHC1)] were studied in the enterocytes of chow-fed hamsters. As shown in FIG. 5, NN extract significantly enhances the mRNA expression of IR, IRS-1, IRS-2, Akt1, PI3Kr1 in enterocytes of chow-fed hamsters; and inhibits SHC1 expression.

Figure 6:
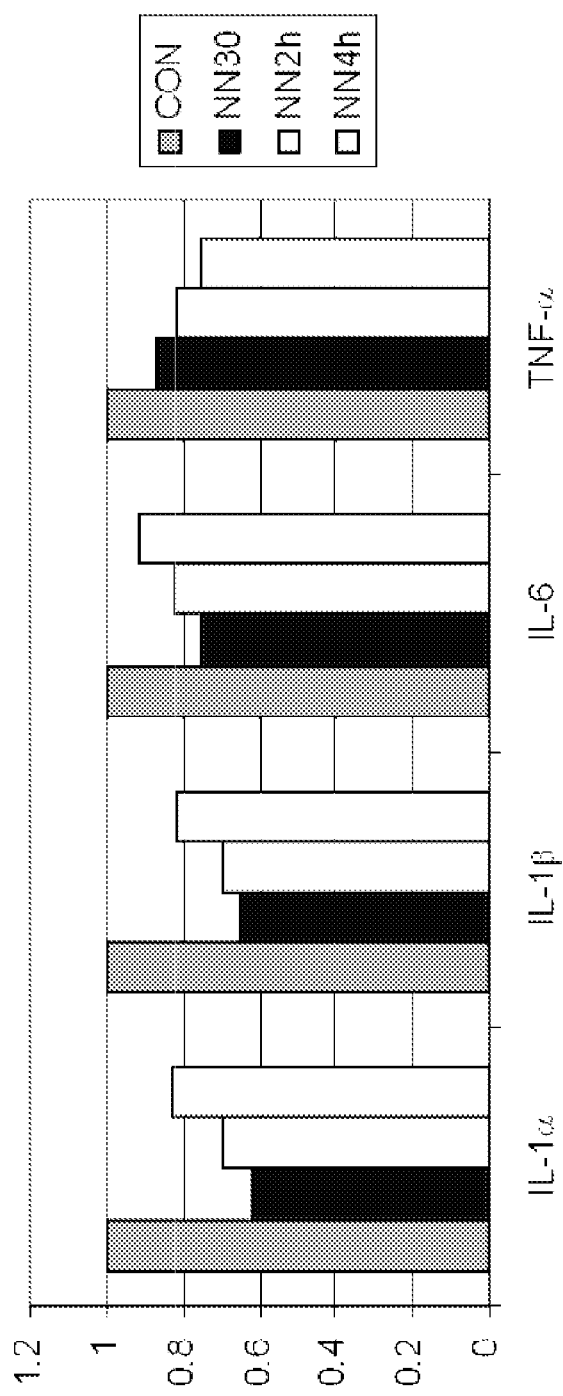
FIG. 6 illustrates that administration of an extract of *Nelumbo nucifera* significantly inhibits the mRNA overexpression of IL-1α, IL-1β, IL-6 and TNF-α in enterocytes of chow-fed hamsters.

We also determined the mRNA levels coding for inflammatory factors components IL-1α, IL-1b, IL-6 and TNF-α in the enterocytes of chow-fed hamsters. As shown in FIG. 6, NN extract significantly inhibits the mRNA overexpression of IL-1α, IL-1β, IL-6 and TNF-α.

Figure 7:
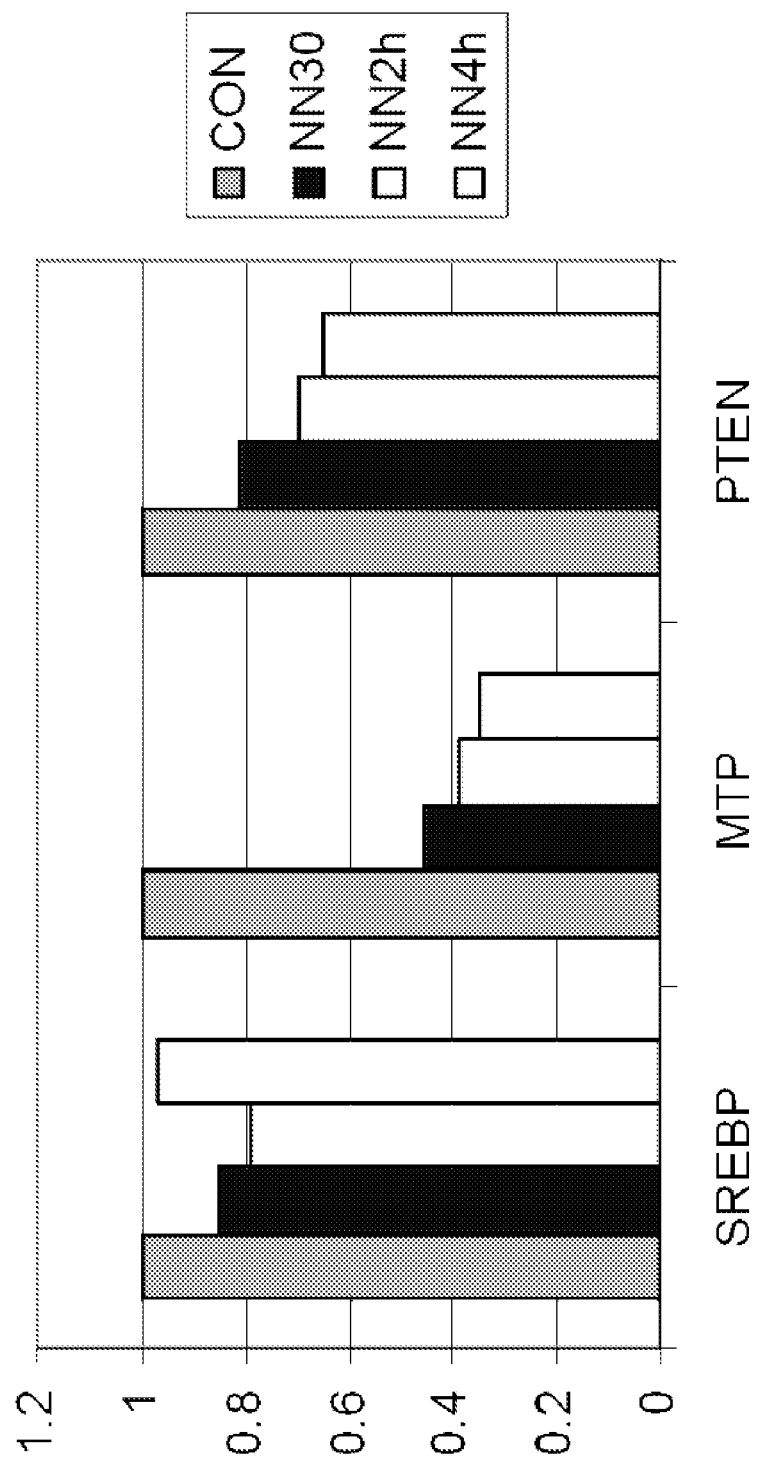
FIG. 7 illustrates that administration of an extract of *Nelumbo nucifera* significantly inhibits the mRNA expression of SREBP1, MTP and PTEN in small intestinal enterocytes from chow-fed hamsters.

We also analyzed the mRNA levels of SREBP1, MTP and PTEN coding for lipids metabolic factors components in the enterocytes of chow-fed hamsters. As shown in FIG. 7, NN extract significantly inhibits the mRNA expression of SREBP1, MTP and PTEN in small intestinal enterocytes from chow-fed hamsters.

Figure 8:
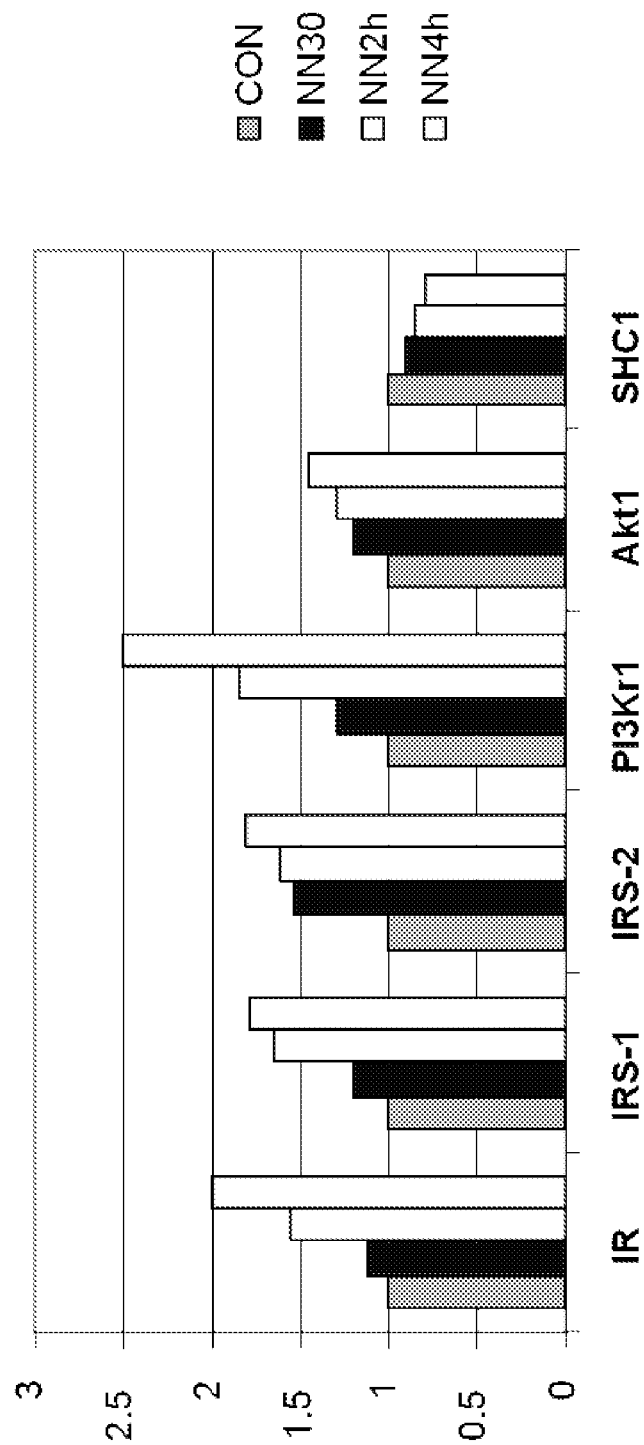
FIG. 8 illustrates that administration of an extract of *Nelumbo nucifera* significantly improves the impaired mRNA overexpression of IR, IRS-1, IRS-2, Akt1, PI3Kr1 in enterocytes of fructose-fed hamsters, and inhibits SHC1 expression.

We also investigated the mRNA levels for insulin signaling pathway genes, IR, IRS-1, IRS-2, Akt1, PI3Kr1, and SHC1 in the enterocytes of hamsters fed a high-fructose diet known to induce insulin resistance. As shown in FIG. 8, NN extract significantly improves the impaired mRNA overexpression of IR, IRS-1, IRS-2, Akt1, PI3Kr1 in enterocytes of fructose-fed hamsters, and inhibits SHC1 expression.

Figure 9:
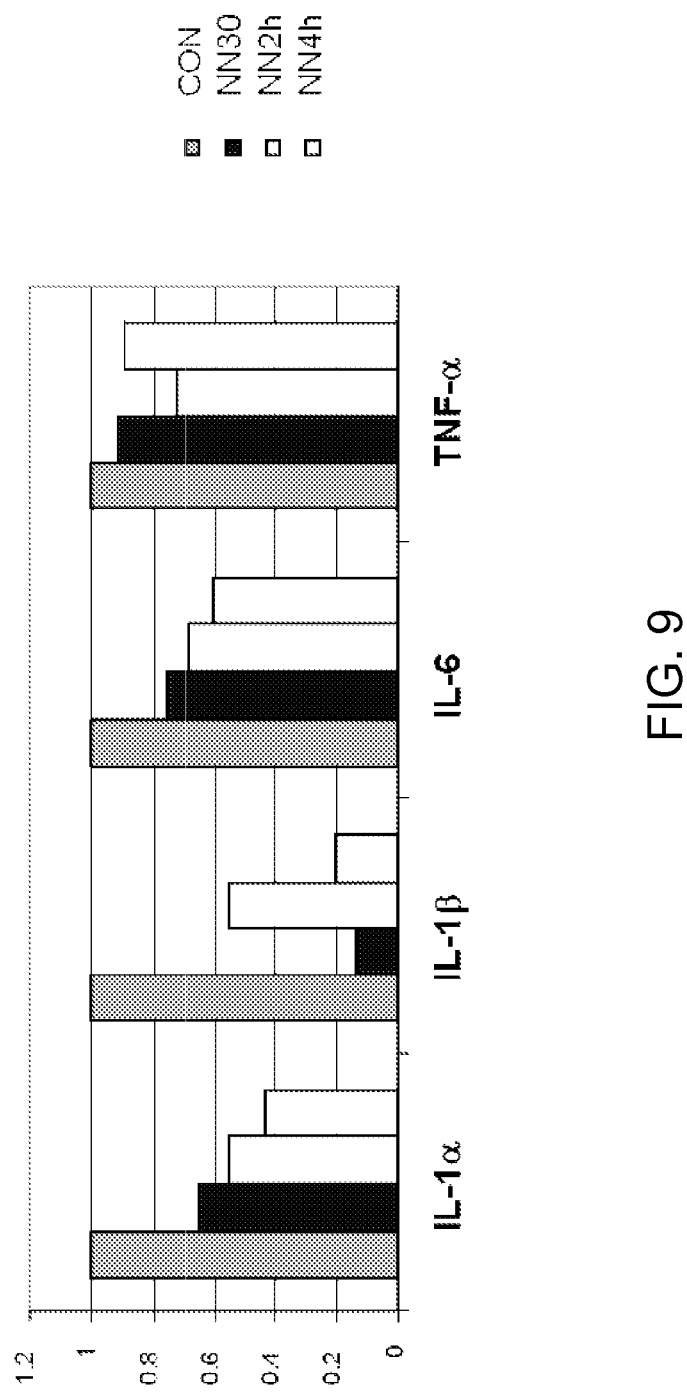
FIG. 9 illustrates that administration of an extract of *Nelumbo nucifera* significantly inhibits the mRNA expression of IL-α, IL-1β, IL-6 and TNF-α in the enterocytes of chow-fed hamsters.

Low-grade systemic inflammation is a prevalent feature of obesity and insulin resistance, and TNF-α may be a key mediator linking inflammation and dysregulation of lipid and glucose metabolism. We have shown TNF-α significantly induces intestinal insulin resistance and apoB48 overproduction in vivo and ex vivo. Here, we determined the mRNA levels of IL-1α, IL-1β, IL-6 and TNF-α coding for inflammatory factors in the enterocytes of chow-fed hamsters. As shown in FIG. 9, NN extract significantly inhibits the mRNA expression of IL-α, IL-1β, IL-6 and TNF-α.

We also measured the mRNA levels for inflammatory factors IL-1β, IL-1α, IL-6 and TNF-α in the enterocytes of fructose-fed hamsters. NN extract significantly inhibits the mRNA overexpression of IL-1α, IL-1α, IL-6 and TNF-α.

Figure 10:
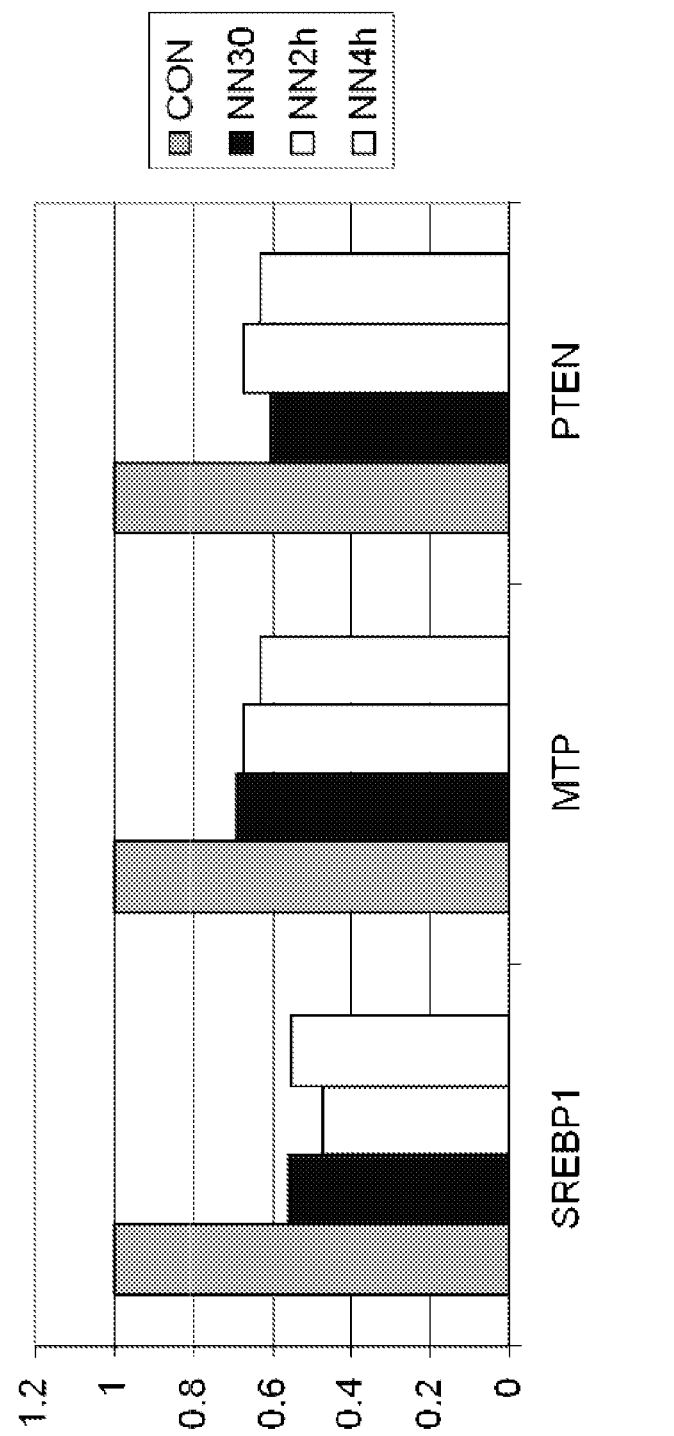
FIG. 10 illustrates that administration of an extract of *Nelumbo nucifera* significantly inhibits the mRNA expression of IL-α, IL-1β, IL-6 and TNF-α in the enterocytes of fructose-fed hamsters.

Insulin resistance and its associated metabolic dyslipidemia result from perturbations in key molecules of the insulin signaling pathway, including overexpression of key phosphatases, and downregulation and/or activation of key protein kinase cascades leading to a state of mixed hepatic insulin resistance and sensitivity. These signaling changes in turn cause an increased expression of SREBP1c, MTP, and PTEN stimulating the intestinal production of apolipoprotein B (apoB)-containing chylomicrons. We tested the mRNA levels for lipid metabolic factors SREBP1, MTP and PTEN in the enterocytes of fructose-fed hamsters. As shown in FIG. 10. NN extract significantly inhibits the mRNA overexpression of SREBP1, MTP and PTEN in small intestinal enterocytes from fructose fed hamsters.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified.

Patents and publications mentioned in the specification are indicative of the levels of those skilled in the art to which the invention pertains. These patents and publications are incorporated herein by reference to the same extent as if each individual application or publication was specifically and individually incorporated herein by reference for the entirety of their teaching.

The foregoing description is illustrative of particular embodiments of the invention, but is not meant to be a limitation upon the practice thereof. The following claims, including all equivalents thereof, are intended to define the scope of the invention.

The invention claimed is:

1. A process of decreasing mRNA levels encoding IL-1α, IL-1β, IL-6, TNF-α, SREBP1, MTP, PTEN or SHC1 and increasing mRNA levels encoding IR, IRS-1, IRS-2, Akt or PI3KrI, in a cell of a subject comprising:
   administering a subject in need thereof, a composition comprising
   a) an effective amount of a water extract of *Nelumbo nucifera* leaf comprising between 1 percent and 30 percent flavonoids,
   b) an extract of cinnamon and
   c) one or more phytosterols.

2. The process of claim 1 wherein said water extract of *Nelumbo nucifera* leaf is administered to said subject at a dose of 100 to 200 milligrams per kilogram of body weight of said subject.

3. The process of claim 1, wherein said water extract of *Nelumbo nucifera* leaf is present in said composition at a concentration of 100 micrograms per milliliter.

4. The process of claim 1 wherein said cell of a subject is an enterocyte.

5. The process of claim 1 wherein the composition is a dietary supplement and wherein said dietary supplement further comprises one or more of a vitamin, a glucose lowering agent, corosolic acid, Momordica, Cecropia, a blood pressure lowering agent, epigallocatechin gallate, or a lipid lowering agent.

6. The process of claim 1 wherein said phytosterol is one or more of policosanol, β-sitosterol, campesterol, stigmasterol, or sitostanol.

7. The process of claim 1 wherein the subject is pre-diabetic or not diabetic.

* * * * *